(12) United States Patent
Huang

(10) Patent No.: US 11,505,824 B2
(45) Date of Patent: Nov. 22, 2022

(54) DIRECT RNA NANOPORE SEQUENCING WITH HELP OF A STEM-LOOP REVERSE POLYNUCLEOTIDE

(71) Applicant: Siemens Healthcare GmbH, Erlangen (DE)

(72) Inventor: Yiwei Huang, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 310 days.

(21) Appl. No.: 16/677,451

(22) Filed: Nov. 7, 2019

(65) Prior Publication Data
US 2020/0149101 A1  May 14, 2020

(30) Foreign Application Priority Data
Nov. 8, 2018  (EP) .................................... 18205148

(51) Int. Cl.
*C12Q 1/6869* (2018.01)
*C12N 15/10* (2006.01)
*C12Q 1/6806* (2018.01)

(52) U.S. Cl.
CPC ......... *C12Q 1/6869* (2013.01); *C12N 15/102* (2013.01); *C12Q 1/6806* (2013.01); *C12N 2310/531* (2013.01)

(58) Field of Classification Search
CPC ................ C12Q 1/6869; C12Q 1/6806; C12N 15/102; C12N 2310/531
See application file for complete search history.

(56) References Cited

U.S. PATENT DOCUMENTS

2009/0023190 A1   1/2009  Lao et al.
2017/0067097 A1*  3/2017  Metzker ............... C12Q 1/6874

FOREIGN PATENT DOCUMENTS

| WO | WO2008102120 |   | 8/2008 |
| WO | WO 2014041337 | * | 3/2014 |
| WO | WO2014041337 |   | 3/2014 |

OTHER PUBLICATIONS

Shchyolkina, A, K. et al: "Parallel-Stranded Oligonucleotides with Alternating d(A-isog)/d(T.C) and d(A.G)/d(T.m 5isoC) Sequences" Nucleosides & Nucleotides, vol. 18, No. 6-7, p. 1555-1562 (Year: 1999).*
Kozarewa, Iwanka and Turner, Daniel J.: "96-Plex Molecular Barcoding for the Illumina Genome Analyzer"; in: Methods in Molecular Biology; vol. 733; pp. 279-298; 2011; DOI 10.1007/978-1-61779-089-8_20.
Agah, Shaghayegh et al.: "DNA Sequencing by Nanopores: Advances and Challenges"; in: Journal of Physics D: Applied Physics; vol. 49; No. 41; 2016.
Shchyolkina, A, K. et al: "Parallel-Stranded Oligonucleotides with Alternating d(A-isog)/d(T.C) and d(A.G)/d(T.m 5isoC) Sequences" Nucleosides & Nucleotides, vol. 18, No. 6-7, Jan. 6, 1999, p. 1555-1562, XP055560166, US.
Bande, Omprakash et al.: "Isoguanine and 5-Methyl-Isocytosine Bases, In Vitro and In Vivo"; in Chemistry A European Journal; vol. 21; No. 13; pp. 5009-5022; 2015; https://doi.org/10.1002/chem.201406392.
Garalde, Daniel R. et al: "Highly Parallel Direct RNA Sequencing on an Array of Nanopores"; Nature Methods, vol. 15, No. 3, Mar. 1, 2018 (Mar. 1, 2018), pp. 201-206, XP055557676, New York ISSN: 1548-7091, DOI: 10.1038/nmeth.4577.
Jonkhout, Nicky et al: "The RNA Modification Landscape in Human Disease", RNA,vol. 23, No. 12; Dec. 16, pp. 1754-1769, XP055516059, US ISSN: 1355-8382, DOI: 10.1261/rna.063503. 117.
Timp, Winston et al.: "Nanopore Sequencing: Electrical Measurements of the Code of Life"; in: IEEE Transactions on Nanotechnology; vol. 9; No. 3; pp. 281-294; 2010; DOI: 10.1109/TNANO. 2010.2044418.
Bande, O. et al.: "Isoguanine and 5-Methyl-Isocytosine Bases, In Vitra and In Vivo",Chemistry A European Journal, vol. 21, No. 13, Feb. 13, 2015 (Feb. 13, 2015), pp. 5009-5022, XP055779852,DE ISSN: 0947-6539, DOI: 10.1002/chem.201406392 Retrieved from the Internet: URL:https://www.ncbi.nlm.nih.gov/pmc/articles/PMC4531829/pdf/chem0021-5009.pdf; 2015.
Horn, T. et al.: "Hybridization Properties of the 5-Methyl-Isocytidine/Isoguanosine Base Pair in Synthetic Oligodeoxynucleotides"; Tetrahedron Letters; Elsevier, Amsterdam, NL; vol. 36, No. 12, Mar. 20, 1995; pp. 2033-2036; XP004028396; ISSN: 0040-4039; DOI: 10.1016/0040-039(95)00230-A; 1995.
Sugiyama, H. et al.: "Remarkably Stable Parallel-Stranded Oligonucleotides Containing 5-Methylisocytosine and Isoguanine"; Journal of the American Chemical Society, American Chemical Society; US vol. 118, No. 41; Oct. 16, 1996; pp. 9994-9995; XP008099315; ISSN: 0002-7863; DOI: 10.1021/JA961371 B; 1996.

(Continued)

*Primary Examiner* — Cynthia B Wilder
(74) *Attorney, Agent, or Firm* — BakerHostetler

(57) ABSTRACT

A method includes (i) providing an RNA polynucleotide; (ii) modifying the RNA polynucleotide by annealing and ligating a polynucleotide comprising a 3' terminal random multimer segment and having a stem-loop form; (iii) optionally performing a reverse transcription of the RNA polynucleotide; (iv) cleaving the stem-loop segment of the annealed polynucleotide to yield a 3' A overhang; (v) connecting an adaptor polynucleotide complex associated with an RNA translocase enzyme and at least one cholesterol tether segment to the polynucleotide obtained in step (iv); (vi) contacting the modified RNA polynucleotide obtained in step (v) with a transmembrane pore such that the RNA translocase controls the movement of the RNA polynucleotide through the transmembrane pore and the cholesterol tether anchors the RNA polynucleotide in the vicinity of the transmembrane pore; and (vii) taking one or more measurements during the movement of the RNA polynucleotide through the transmembrane pore Other features are also disclosed.

8 Claims, 3 Drawing Sheets
Specification includes a Sequence Listing.

(56) References Cited

OTHER PUBLICATIONS

Yang, L. et al.: "Universal Stem-Loop Primer Method for Screening and Quantification of MicroRNA"; PLoS ONE; vol. 9, No. 12; Dec. 30, 2014; p. e115293; XP055517341; DOI: 10.1371/journal.pone. 0115293; 2014.

* cited by examiner

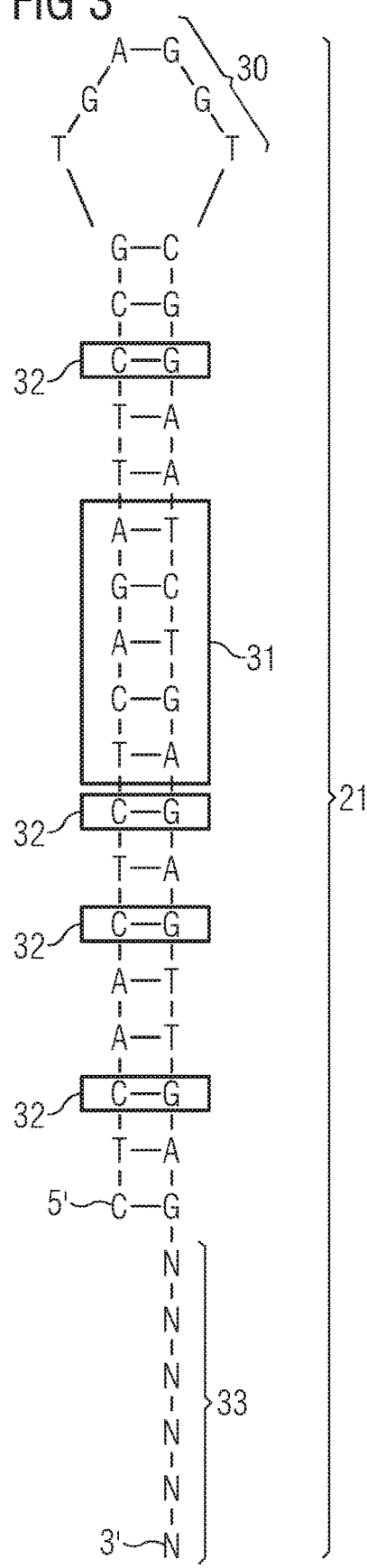

SEQUENCE LISTING

```
<160> NUMBER OF SEQ ID NOS: 3

<210> SEQ ID NO 1
<211> LENGTH: 17
<212> TYPE: RNA
<213> ORGANISM: Homo sapiens

<400> SEQUENCE: 1
aaaaaaaaaa aaaaaaa                                                 17

<210> SEQ ID NO 2
<211> LENGTH: 17
<212> TYPE: DNA
<213> ORGANISM: Artificial Sequence
<220> FEATURE:
<223> OTHER INFORMATION: Extended poly-T oligonucleotide

<400> SEQUENCE: 2
tttttttttt ttttttt                                                 17

<210> SEQ ID NO 3
<211> LENGTH: 48
<212> TYPE: DNA
<213> ORGANISM: Artificial Sequence
<220> FEATURE:
<223> OTHER INFORMATION: Stem-loop primer with random multimer
<220> FEATURE:
<221> NAME/KEY: misc_feature
<222> LOCATION: (43)..(48)
<223> OTHER INFORMATION: n is a, c, g, or t

<400> SEQUENCE: 3
ctcaactctc agattccgtg aggtcggaat ctgagagttg agnnnnnn               48
```

DIRECT RNA NANOPORE SEQUENCING WITH HELP OF A STEM-LOOP REVERSE POLYNUCLEOTIDE

CROSS REFERENCE TO RELATED APPLICATION

This claims priority to European Patent Application No. EP 18205148.2, filed Nov. 8, 2018, which is hereby incorporated by reference herein in its entirety for all purposes.

FIELD

The present invention relates to a method of characterizing a target RNA polynucleotide.

BACKGROUND

The general goal of transcriptomics is to fully sequence all transcriptional species in a sample, determine the transcriptional structure of a gene, including splice variants and fusion genes, quantify changes in the expression levels of transcripts at different stages of development and in different environments, and determine antisense transcription occurs in biological cells. The most widely used strategies for next-generation RNA-sequencing include poly-T priming or ribonucleic acid (RNA) fragmentation followed by random hexamer initiation of synthetically complementary DNA (cDNA). These cDNA strands are then usually prepared for analysis on a given sequencing system using library preparation methods that include PCR. However, which type of PCR is used in the preparation of a library will introduce bias. For example, the resulting library will be less complex than the total amount of mRNA because not all transcripts will be amplified with the same efficiency, leading to the exit of certain RNA species and over-amplification of other species. In addition, PCR amplification generates a synthetic copy of the original RNA strand and potential epigenetic information may be lost. Therefore, there is a clear need for largely avoiding the amplification of RNA molecules during library preparations for sequencing purposes.

Exceptions to PCR-based library preparations include FRT-Seq on the Illumina platforms, where the first-strand cDNA synthesis reaction is performed on single strands of RNA hybridized to the flow cell surface. Another example is direct RNA sequencing on the Helicos platform, which is a sequencing-by-synthesis reaction using native RNA strands as a template. In both cases, PCR amplification is avoided, removing this source of distortion, thus the data obtained more faithfully reflect the abundance of RNAs in the original sample. However, these approaches are still based on synthetic copies of the original RNA strand so that information about modifications is not preserved. Both approaches, in addition, necessarily produce short sequence reads, which is somewhat disadvantageous since transcripts in eukaryotes typically undergo alternative splicing, producing several different isoforms, e.g., with different transcription start sites, coding sequences, and untranslated regions. Short read sequencing, however, is typically unable to span entire transcripts and may miss new splice variants.

A new direct RNA sequencing approach has been developed by Oxford Nanopore Technologies. This approach, which is also depicted in FIG. 1 is based on an annealing of a poly-T primer to a poly-A-tail of mRNA molecules. It hence only and exclusively works with RNA molecules having a poly-A tail and excludes all other RNA molecules.

There is hence a need for an improved direct RNA sequencing methodology allowing to sequence all RNA species, i.e., also those RNA molecules which do not possess a poly-A-tail.

SUMMARY

The present invention addresses this need and provides a method of characterizing a target RNA polynucleotide comprising: (i) providing an RNA polynucleotide; (ii) modifying the RNA polynucleotide by annealing and ligating a polynucleotide comprising a 3' terminal random multimer segment and having a stem-loop form; (iii) optionally performing a reverse transcription of the RNA polynucleotide; (iv) cleaving the stem-loop segment of the annealed polynucleotide to yield a 3' A overhang; (v) connecting an adaptor polynucleotide complex associated with an RNA translocase enzyme and at least one cholesterol tether segment to the polynucleotide obtained in step (iv); (vi) contacting the modified RNA polynucleotide obtained in step (v) with a transmembrane pore such that the RNA translocase controls the movement of the RNA polynucleotide through the transmembrane pore and the cholesterol tether anchors the RNA polynucleotide in the vicinity of the transmembrane pore; and (vii) taking one or more measurements during the movement of the RNA polynucleotide through the transmembrane pore, wherein the measurements are indicative of one or more characteristics of the RNA polynucleotide, thereby characterizing the target RNA polynucleotide.

The present invention also provides a kit for characterizing a target RNA polynucleotide, as well as a use of a polynucleotide comprising a 3' terminal random multimer segment and having a stem-loop form for the modification of an RNA polynucleotide.

The presented method, being based on random multimer sequences, advantageously allows to perform direct RNA sequencing with all RNA species, not only those which comprise poly-A-tails, i.e., mRNAs. Accordingly, also mRNA fragments of different origins may be sequenced. The stem-loop polynucleotide further allows for a stabilization of the transcript and allows for the presentation of the random multimer at the 3' end of the stem-loop polynucleotide. Further, the presence of a restriction enzyme recognition site in the stem-loop polynucleotide further allows for a cleavage of the polynucleotide yielding a 3' A overhang, which can subsequently be used for the connection of an adaptor polynucleotide complex associated with an RNA translocase enzyme necessary for translocating the RNA molecule through a transmembrane pore in order to obtain its sequence.

In a further aspect, the present invention relates to a method of preparing a target RNA polynucleotide for transmembrane sequencing comprising: (i) providing an RNA polynucleotide; (ii) modifying the RNA polynucleotide by annealing and ligating a polynucleotide comprising a 3' terminal random multimer segment and having a stem-loop form; (iii) optionally performing a reverse transcription of the RNA polynucleotide; (iv) cleaving the stem-loop segment of the annealed polynucleotide to yield a 3' A overhang; and (v) connecting an adaptor polynucleotide complex associated with an RNA translocase enzyme and at least one cholesterol tether segment to the polynucleotide obtained in step (iv).

In one embodiment of the above mentioned methods, the polynucleotide comprising a 3' terminal random multimer segment and having a stem-loop form is a DNA polynucleotide comprising one or more non-DNA nucleotides.

It is preferred that the polynucleotide comprising a 3' terminal random multimer segment and having a stem-loop form comprises one or more 5-methyl-isoC-isoG base-pairs.

In a further embodiment, the 5-methyl-isoC-isoG base-pairs are provided at least at every $4^{th}$, $5^{th}$ or $6^{th}$ position of the stem-loop polynucleotide.

In yet another embodiment, the 5-methyl-isoC-isoG base-pairs are provided at least at every $4^{th}$, $5^{th}$ or $6^{th}$ position of the stem-loop polynucleotide.

In a further embodiment of the present invention, the random multimer segment is a random hexamer, random heptamer, random octamer, random nonamer or random decamer segment. It is preferred that the random multimer segment is a random hexamer segment.

According to another embodiment of the present invention, the polynucleotide comprising a 3' terminal random multimer segment and having a stem-loop form comprises a restriction enzyme recognition site of the sequence 5'-ACAGT-3' or 5'-TCAGA-3'.

In a further embodiment, the enzyme Hpy188I is used to cleave the restriction enzyme recognition site 5'-TCAGA-3'; or the enzyme Bst4CI, HpyCH4III or TaaI is used to cleave the restriction enzyme recognition site 5'-ACAGT-3'.

In yet another embodiment, the polynucleotide comprising a 3' terminal random multimer segment and having a stem-loop form additionally comprises a barcoding section.

In another embodiment of the present invention, the one or more characteristics of the RNA polynucleotide which are measured during the translocation of the RNA polynucleotide through the transmembrane pore, are (i) length of the RNA polynucleotide, (ii) identity of the RNA polynucleotide, (iii) sequence of the RNA polynucleotide, and (iv) presence of a nucleotide modification in the RNA polynucleotide. It is preferred that the characteristic to be measured is the sequence of the RNA polynucleotide.

In a further embodiment, the RNA polynucleotide is any RNA polynucleotide. In specific embodiments, it is mRNA, a fragment of mRNA, pre-mRNA, ncRNA, rRNA, miRNA, snoRNA, srRNA, tmRNA, siRNA or piRNA.

In another embodiment according to the present invention, the RNA translocase is SF2 helicase, NS3 helicase, NPH-II helicase, Upf1 helicase or RIG-I translocase or derivatives thereof, or a derivative of a DNA helicase such as Hel308 helicase, RecD helicase, XPD helicase or Dda helicase which is capable of translocating RNA polynucleotides.

According to a further embodiment, the transmembrane pore protein is a pore protein derived from hemolysin, leukocidin, MspA, MspB, MspC, MspD, CsgG, lysenin, outer membrane porin F (OmpF), outer membrane porin G (OmpG), outer membrane phospholipase A, Neisseria autotransporter lipoprotein (NalP) or WZA.

In another aspect, the present invention relates to a kit for characterizing a target RNA polynucleotide comprising a polynucleotide comprising a 3' terminal random multimer segment and having a stem-loop form, wherein the stem-loop form comprises one or more 5-methyl-isoC-isoG base-pairs, preferably comprising a polynucleotide with a 3' terminal random multimer segment and having a stem-loop form as defined herein.

In yet another aspect, the present invention relates to a use of a polynucleotide comprising a 3' terminal random multimer segment and having a stem-loop form, wherein the stem-loop form comprises one or more 5-methyl-isoC-isoG base-pairs for the modification of an RNA polynucleotide, thereby preparing the RNA polynucleotide for a direct RNA sequencing through a transmembrane pore.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

The following figures are provided for illustrative purposes. It is thus understood that the figures are not to be construed as limiting. The skilled person in the art will clearly be able to envisage further modifications of the principles laid out herein.

FIG. 3 shows an example of a stem-loop form-comprising polynucleotide according to an embodiment of the present invention.

DETAILED DESCRIPTION

Figure 1:
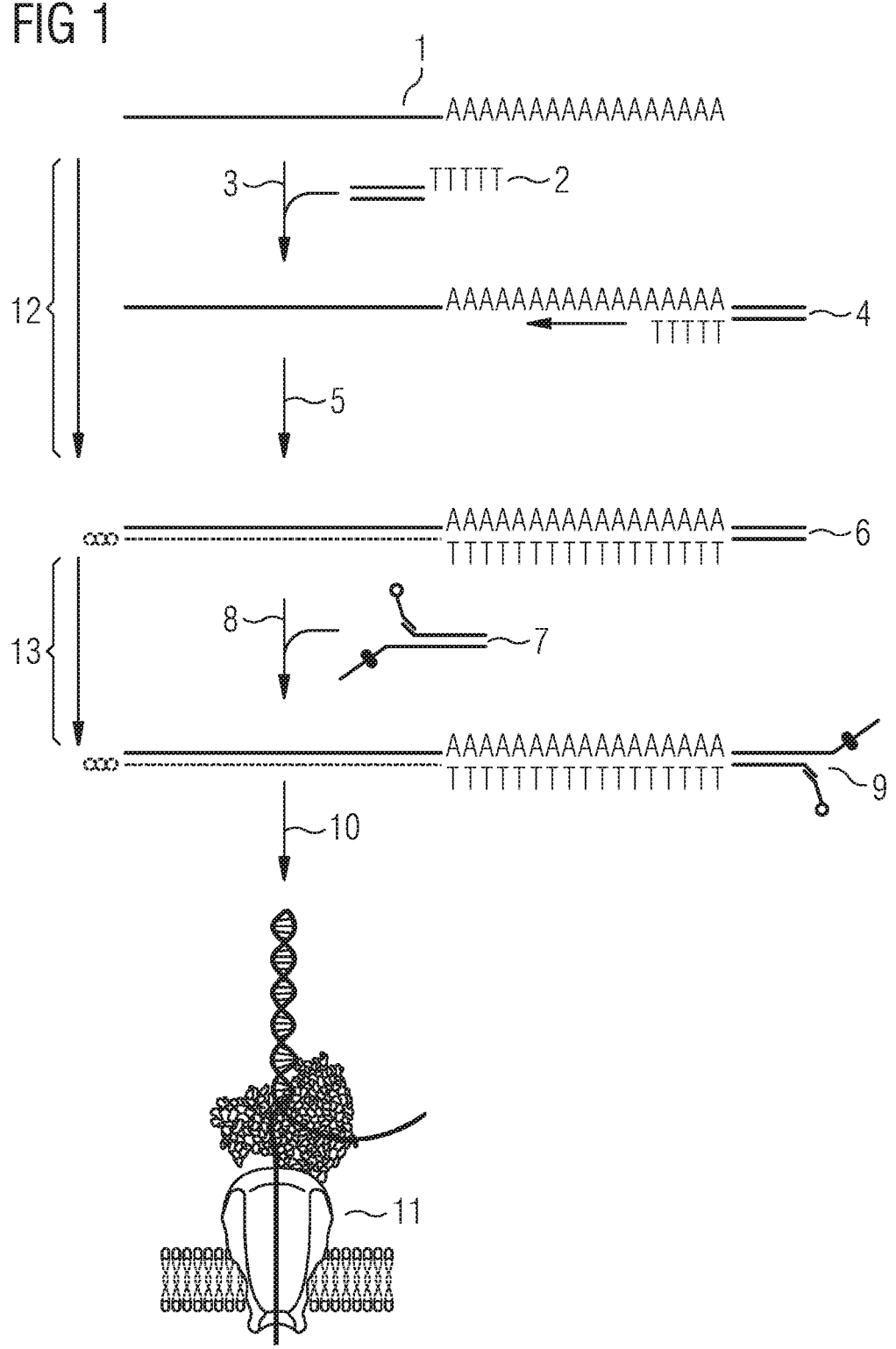
FIG. 1 shows a schematic illustration of an RNA sequencing approach limited to RNA polynucleotides comprising poly-A-tails.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" or "essentially consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "(i)", "(ii)", "(iii)" or "(a)", "(b)", "(c)", "(d)", or "first", "second", "third", etc., and the like in the description or in the claims, are used for distinguishing between similar elements and not necessarily for describing a sequential or chronological order.

It is to be understood that the terms so used are interchangeable under appropriate circumstances and that the embodiments of the invention described herein are capable of operation in other sequences than described or illustrated herein. In case the terms relate to steps of a method, procedure or use there is no time or time interval coherence between the steps, i.e., the steps may be carried out simultaneously or there may be time intervals of seconds, minutes, hours, days, weeks, etc., between such steps, unless otherwise indicated.

It is to be understood that this invention is not limited to the particular methodology, protocols, etc., described herein as these may vary. It is also to be understood that the terminology used herein is for the purpose of describing particular embodiments only, and is not intended to limit the scope of the present invention that will be limited only by the appended claims.

The drawings are to be regarded as being schematic representations and elements illustrated in the drawings are not necessarily shown to scale. Rather, the various elements are represented such that their function and general purpose become apparent to a person skilled in the art.

Unless defined otherwise, all technical and scientific terms used herein have the same meanings as commonly understood by one of ordinary skill in the art.

As has been set out above, the present invention concerns in one aspect a method of characterizing a target RNA polynucleotide comprising (i) providing an RNA polynucleotide; (ii) modifying the RNA polynucleotide by annealing and ligating a polynucleotide comprising a 3' terminal random multimer segment and having a stem-loop form; (iii) optionally performing a reverse transcription of the RNA polynucleotide; (iv) cleaving the stem-loop segment of the annealed polynucleotide to yield a 3' A overhang; (v) connecting an adaptor polynucleotide complex associated with an RNA translocase enzyme and at least one cholesterol tether segment to the polynucleotide obtained in step (iv); (vi) contacting the modified RNA polynucleotide obtained in step (v) with a transmembrane pore such that the RNA translocase controls the movement of the RNA polynucleotide through the transmembrane pore and the cholesterol tether anchors the RNA polynucleotide in the vicinity of the transmembrane pore; and (vii) taking one or more measurements during the movement of the RNA polynucleotide through the transmembrane pore, wherein the measurements are indicative of one or more characteristics of the RNA polynucleotide, thereby characterizing the target RNA polynucleotide.

In a first step of the method of the present invention thus an RNA polynucleotide is provided.

As used herein, the term "RNA polynucleotide" or "target RNA polynucleotide" relates to any macromolecule comprising two or more ribonucleotides. Ribonucleotides typically contain a nucleobase, a ribose sugar, and at least one phosphate group. The nucleobases are typically adenine, guanine, cytosine, and uracil. RNA polynucleotides are typically single-stranded molecules, and can, however, also be provided in a double-stranded form by partial complementary base pairing. The RNA polynucleotide typically does not form long double helical stretches. The RNA polynucleotide may be naturally occurring or artificial. It may comprise, in addition to the elements mentioned above, modifications such as oxidized or methylated nucleotides. The RNA polynucleotide may also, in certain embodiments, comprise artificial additions such as tags or labels.

The RNA polynucleotide may be of any possible origin, e.g., prokaryotic, eukaryotic, archaeal or viral. The RNA polynucleotide to be characterized according to the present invention may have any known possible biological or cellular function. For example it may be any naturally occurring or synthetic polynucleotide such as messenger RNA (mRNA), ribosomal RNA (rRNA), heterogenous nuclear RNA (hnRNA), transfer RNA (tRNA), transfer messenger RNA (tmRNA), micro RNA (miRNA), small nuclear RNA (snRNA), spliced leader RNA (SL RNA), small nucleolar RNA (snoRNA), antisense RNA (asRNA), guide RNA (gRNA), long noncoding RNA (lncRNA), small interfering RNA (siRNA), Piwi-interacting RNA (piRNA), trans-acting RNA (tasiRNA), precursor mRNA (pre-mRNA) or repeat associated siRNA (rasiRNA). The RNA species mentioned typically differ in terms of size, nucleotide composition, folding status and presence or absence of 3' extensions. For example, mRNA molecules in eukaryotes typically comprise a 3' poly-A tail which consists of multiple adenosine monophosphates and is attached to the molecules after transcription by a polyadenylate polymerase. Other RNA species or fragments of eukaryotic mRNAs may not comprise such an elongation. For example, precursor mRNAs (pre-mRNAs) are non-processed mRNA molecules comprising intron sequences which have not yet been modified by the polyadenylate polymerase. In a preferred embodiment, the target RNA polynucleotide is an mRNA, a fragment of an mRNA, pre-mRNA molecule, an ncRNA, a miRNA, an snoRNA, a tmRNA, an siRNA or a piRNA. It is particularly preferred that the target RNA is an RNA polynucleotide which does not comprise a poly-A tail or an oligo-A tail at the 3' end. For example, fragments of mRNA polynucleotides which do not comprise the mRNA 3' portion typically do not comprise a poly-A tail. Also pre-mRNA molecules typically do not comprise a poly-A tail. Similarly, RNA polynucleotide species which do not belong to the group of eukaryotic mRNAs typically do not comprise poly-A extensions. Such species are preferred targets since the method of the invention is capable of characterizing these polynucleotides because it does not require the existence of a poly-A extension. In certain embodiments, the target RNA polynucleotide may also be a typical eukaryotic mRNA molecule, which can also be characterized according to the present invention.

The provision of the RNA polynucleotide may include the extraction and/or purification of the RNA molecule, e.g., by guanidine-isothiocyanate lysis, separation from cell debris, filtration, elution from a column, e.g., silica membrane columns, centrifugation, digestion, e.g., DNase digestion, or removal or nucleotide or protein components in a sample, etc. It is preferred that the RNA polynucleotide is provided in a buffer solution comprising any suitable ingredient preventing RNA degradation. The buffer may, for example, be an RNAse-free $H_2O$ buffer comprising EDTA (e.g. 0.1 mM) or a TE buffer (10 mM Tris, 1 mM EDTA). The buffer may preferably comprise RNAse blocking compounds or RNase inhibitors such as RNaseZap™, SUPERaseIN™, RNaseOUT™, ribonuclease inhibitor, RNasin® or the like.

In further embodiments, the provision of RNA polynucleotides may also include the employment of suitable conditions to keep the RNA molecule or a part of it in a single stranded form. Such conditions may include the use of a certain temperature or range of temperatures before or during the performance of the methods of the invention, and/or the use of specific buffers or salt conditions in order to avoid the formation of secondary structures in the RNA molecule. It is preferred that the RNA polynucleotide or a part of it is made single stranded by a short heating denaturation. This short heating denaturing may, for example, be applied when annealing a polynucleotide comprising a 3' terminal random multimer segment and having a stem-loop form as described herein.

The provision of RNA polynucleotides may also involve the taking of samples from a subject and their processing, e.g., extraction of RNA or preparatory steps facilitating the extraction of RNA. The term "sample from a subject" as used herein relates to any biological material obtained via suitable methods known to the person skilled in the art from a subject. The sample used in the context of the present invention should preferably be collected in a clinically acceptable manner, more preferably in a way that RNA polynucleotides are preserved. The biological samples may include body tissues and/or fluids, such as blood, or blood components like serum or plasma, sweat, sputum or saliva, semen and urine, as well as feces or stool samples. Furthermore, the biological sample may contain a cell extract derived from or a cell population including an epithelial cell, preferably a neoplastic epithelial cell or an epithelial cell derived from tissue suspected to be neoplastic. Alternatively, the biological sample may be derived from the environment, e.g., from the soil, a lake, a river, etc., or from animal sources.

In certain embodiments, cells may be used as primary sources for RNA polynucleotides. Accordingly, the cells may be purified from obtained body tissues and fluids if necessary, and then further processed to obtain RNA polynucleotides. In certain embodiments, samples, in particular after initial processing, may be pooled. The present invention preferably envisages the use of non-pooled samples.

In a specific embodiment of the present invention, the content of a biological sample may also be submitted to an enrichment step. For instance, a sample may be contacted with ligands specific for the cell membrane or organelles of certain cell types, functionalized for example with magnetic particles. The material concentrated by the magnetic particles may subsequently be used for the extraction of RNA polynucleotides. In further embodiments of the invention, biopsy or resections samples may be obtained and/or used. Such samples may comprise cells or cell lysates. Furthermore, cells, e.g., tumor cells, may be enriched via filtration processes of fluid or liquid samples, e.g., blood, urine, sweat, etc. Such filtration processes may also be combined with enrichment steps based on ligand specific interactions as described herein above.

In a next step of the method of the invention, the RNA polynucleotide as mentioned above is modified. The modification is firstly an annealing with a polynucleotide comprising a 3' terminal random multimer segment and having a stem-loop form. The term "annealing a polynucleotide" as used herein relates to the pairing of the single stranded RNA polynucleotide with a complementary single stranded polynucleotide by hydrogen bonds to form a double-stranded polynucleotide. The complementary polynucleotide may either be an RNA molecule or a DNA polynucleotide. It may further comprise one or more modifications such as comprising one or more non-naturally occurring nucleotides, chemical modifications to the nucleotides, the presence of tag or spacer elements, etc. It is preferred that the complementary polynucleotide is a DNA polynucleotide or a modified DNA polynucleotide.

The annealing polynucleotide may have any suitable overall size or length, e.g., it may have an overall length of about 20 to 100 nucleotides, preferably an overall length of about 25 to 75 nucleotides, more preferably an overall length of about 30 to 50 nucleotides, e.g., 30, 35, 40, 45 or 50 nucleotides, or any overall length in between the mentioned values.

The term "3' terminal random multimer" as used herein means that the complementary region, which is capable of annealing with the RNA polynucleotide, has a multimeric random sequence at the 3' end. The corresponding segment is typically single stranded and thus capable of forming hydrogen bonds leading to a double-stranded polynucleotide comprising the RNA polynucleotide and the second polynucleotide annealed to it. Such random segments may comprise between 5 and 15 nucleotides with a random base sequence, i.e., without a predefined sequence. The random base sequence typically covers all sequence possibilities in the covered stretch, including mono-nucleotide stretches such as poly-T, poly-A, poly-G, poly-C. Accordingly, the polynucleotide is used as a group of different polynucleotides to cover all possibilities. The number of different polynucleotides used for the annealing step depends on the size of the sequence covered with longer sequences necessitating more different polynucleotides to cover all possible sequence variations than shorter sequences. It is preferred that the random segment comprises 6, 7, 8, 9, or 10 nucleotides, i.e., that the random segment is a hexamer, heptamer, octamer, nonamer or decamer. It is particularly preferred to use 6 nucleotides (hexamers). The presence of the random multimer allows to anneal with any RNA polynucleotide present irrespective of the sequence of the RNA polynucleotide or the presence of a poly-A tail. It is hence, advantageously, possible to characterize not only mRNA molecules, but also non-poly-A fragments thereof, as well as any other RNA molecule.

The term "stem-loop form" as used herein means that the polynucleotide annealed to the RNA polynucleotide comprises in the sector adjacent to the random multimer segment a partially double-stranded segment which comprises a double stranded stem sector and a hairpin or hairpin loop sector connecting the double stranded sectors. The stem part thus typically comprises two regions of the same strand, which are complementary in nucleotide sequence when read in opposite directions. These segments can base-pair and form a double helix that ends in an unpaired loop.

Without wishing to be bound by theory, it is believed that the formation of a stem-loop structure is dependent on the stability of the resulting helix and loop regions. The first prerequisite is typically the presence of a sequence that can fold back on itself to form a paired double helix. The stability of this helix may predominantly be determined by its length, the number of mismatches or bulges it may contain, and the base composition of the paired region. Since pairings between guanine and cytosine have three hydrogen bonds they are more stable in comparison to adenine-thymine pairings, which have only two. In certain embodiments, the stem segment comprises more guanine-cytosine pairings than adenine-thymine pairings.

Furthermore, the stability of the loop may have an influence on the formation of the stem-loop structure. It is preferred that the hairpin loop is not smaller than three bases, e.g., is 4, 5, 6, 7, 8 or more bases long. It is further preferred that the loops are not longer than about 10 to 12 bases since large loops typically tend to be unstable. In certain embodiments, the loop may have a size of more than 12 bases and showing a further secondary structure such as a pseudoknot. It is particularly preferred that the loop has a length of about 4-8 bases. In some embodiments, the loop has the sequence 5'-TNCG-3', i.e., it is a tetraloop which is stabilized due to the base-stacking interactions of its component nucleotides.

In preferred embodiments of the present invention, the stem-loop form is stabilized by the presence of non-DNA nucleotides in the polynucleotide. The term "non-DNA nucleotide" as used herein relates to artificial nucleotides which are not naturally occurring. It is preferred that the artificial nucleotides convey a base-pairing which is stronger than cytosine-guanine and adenine-thymine. Examples of such nucleotides are 5-methyl-iso-cytosin and iso-guanin. Further details on these nucleotides are known to the skilled person or can be derived from suitable literature sources such as Bande et al., Chem. Eur. J., 2015, 21, 5009-5022. According to embodiments of the invention, the polynucleotide which anneals via its random multimer to a target RNA polynucleotide comprises one or more 5-methyl-iso-cytosin and iso-guanin nucleotides positioned in a way to allow a base-pairing. It is preferred that the base-pairing results in the presence of a hairpin loop as described above, preferably a hairpin loop of 4 to 8 bases.

In further preferred embodiments, the stem-loop segment of the annealing polynucleotide according to the present invention comprises 2, 3, 4, 5, 6, 7, 8, 9, 10 or more 5-methyl-iso-cytosin and iso-guanin base-pairings. Typically, such base-pairings may be provided at certain distances from each other. For example, the stem-loop segment of the annealing polynucleotide according to the present invention may be designed such that 5-methyl-iso-cytosin and iso-guanin base-pairings occur every $4^{th}$, $5^{th}$, or $6^{th}$ position of the stem-loop segment. Also envisaged are different distances such as a presence of the 5-methyl-iso-cytosin and iso-guanin base-pairings every $2^{nd}$, $3^{rd}$, or, in case of longer structures, every $7^{th}$, $8^{th}$, or $9^{th}$ position of the stem-loop segment. The positions may further be modified, e.g., 2 or more, e.g., 2, 3, or 4 5-methyl-iso-cytosin and iso-guanin base-pairings may be grouped followed by a stretch of no such base-pairings, followed by a single 5-methyl-iso-cytosin and iso-guanin base-pairing or another group of 2 or more base-pairings, etc. It is preferred that the 5-methyl-iso-cytosin and iso-guanin base-pairings are designed such that they are capable of avoiding damage to the random multimer when binding to RNA polynucleotides as described herein. The base-pairings in the stem-loop segment which are not 5-methyl-iso-cytosin and iso-guanin base-pairings may be G-C or A-T, or A-U base-pairings. It is preferred that the base-pairings are G-C base-pairings.

The modification of the RNA polynucleotide as mentioned above is, after the annealing, secondly a ligation of the annealed polynucleotide comprising a 3' terminal random multimer segment and having a stem-loop form as described above to the RNA polynucleotide. The ligation takes place at the 5' end of the annealed polynucleotide. Accordingly, the present invention envisages that the 5' end of the polynucleotide comprises a phosphate residue. This phosphate residue may, in certain embodiments, e.g., when it is not present, be added to the polynucleotide via the activity of a phosphorylating enzyme. Examples of suitable enzymes are a kinase such as T4 polynucleotide kinase.

The ligation may be a chemical or an enzymatic ligation. A chemical ligation typically requires the presence of condensing reagents. An example of a chemical ligation envisaged by the present invention makes use of electrophilic phosphorothioester groups. Further examples include the use of cyanogen bromide as a condensing agent.

The enzymatic ligation between the RNA polynucleotide to be characterized and the annealed polynucleotide comprising a 3' terminal random multimer segment and having a stem-loop form as described above may, for example, subsequently be performed with any suitable enzymatic ligase known to the skilled person. Examples of suitable ligases include T4 DNA ligase. Alternatively, ligases such as E. coli DNA ligase, Taq DNA ligase, Tma DNA ligase, 9° N DNA ligase, T4 Polymerase 1, T4 Polymerase 2, or Thermostable 5' App DNA/RNA ligase may be used.

For the phosphorylation and/or the ligation to work properly, suitable buffer conditions and the presence of suitable ingredients are provided. For example, for the phosphorylation ATP (e.g. 1 mM) has to be provided. A suitable buffer may further comprise Tris-HCl, e.g., in a concentration of 50 mM, $MgCl_2$, e.g., in a concentration of 10 mM, and DTT, e.g., in a concentration of 10 mM. The pH may be adjusted to 7.8.

For the ligation, for example, a T4 DNA ligase buffer, ATP, e.g., in an amount of 10 mM, and PEG, e.g., 50% PEG8000 may be provided. For different ligases, the conditions may be changed, e.g., in accordance with the manufacturer's indications.

The method of the present invention typically does not comprise target polynucleotide amplification or reverse transcription in order to reduce the amount of workflow needed to characterize target RNA polynucleotide.

In certain embodiments, the step of reverse transcription may however, optionally, be performed in order to obtain an RNA-cDNA construct which is capable of stabilizing the RNA polynucleotide, e.g., by avoiding RNA secondary or tertiary structures, etc. The present invention thus envisages in these embodiments the reverse transcription of the RNA polynucleotide starting from the annealed polynucleotide comprising a 3' terminal random multimer segment and having a stem-loop form. The reverse transcription may be performed with any suitable reverse transcriptase known to the skilled person. Examples of such suitable reverse transcriptases are reverse transcriptases which do not comprise an RNase H-activity. Specific examples include MMLV reverse transcriptase without RNase H activity or commercially available reverse transcriptases such as SuperScriptγγ™, SuperScript II™, SuperScript III™, StrataScript® etc.

The reverse transcriptase reaction is performed with or in the presence of a suitable buffer. Such a buffer may, for example, comprise TrisHCL, e.g., in a concentration of 250 mM, KCl, e.g., in a concentration of 375 mM, $MgCl_2$, e.g., in a concentration of 15 mM and DTT, e.g., in a concentration of 0.1 M, preferably at a pH of 8.3. In addition, a suitable amount of dNTPs, e.g., dATP, dCTP, cGTP and cTTP has to be used, e.g., in a suitable concentration such as 10 mM.

In a next step of the method according to the invention, the stem-loop segment of the annealed polynucleotide is cleaved. The term "cleaving" or "cleavage" as used herein refers to a double-stranded cut, i.e., an incision trough each strand, in a double stranded nucleic acid molecule, typically performed by a restriction enzyme or restriction endonuclease.

The cleavage may be performed by any suitable restriction enzyme. The cleavage may take place at any suitable position within the stem-loop segment. Typically, the cleavage may take place in the stem portion of the stem-loop segment. By cutting the stem portion of the stem-loop segment any suitable ending at the cleaved site may be produced. Such an ending may either be a sticky ending, i.e., comprising a 5' or 3' overhang, or it may be a blunt end, i.e., having no overhang. It is preferred that a sticky ending is obtained. It is further preferred that the sticky end is a 3' overhang. According to specific embodiments, the overhang may have any suitable length, e.g., 1, 2, 3, 4, 5, 6 or more nucleotides. In particularly preferred embodiments, the overhang is a 1 nucleotide 3' overhang. The invention further specifically envisages that the 3' overhang is a 1 nucleotide A overhang.

The cleavage may be performed under any suitable conditions. For example, the restriction enzyme used may be employed in a suitable buffer. For example, such a buffer may comprise NaCl, e.g., 50 mM, TrisHCl, e.g., 10 mM, $MgCl_2$, e.g., 10 mM, and BSA, e.g., 100 µg/ml; or potassium acetate, e.g., 50 mM, Tris-acetate, e.g., 20 mM, Mg-acetate, e.g., 10 mM, and BSA, e.g., 100 µg/ml, bis-Tris-propane-HCl, e.g., 10 mM, MgCl$_2$, e.g., 10 mM, and BSA, e.g., 100 µg/ml. The buffer may, for example, have a pH of 7.9.

In a specific group of embodiments, the cleavage is performed at the restriction enzyme recognition site 5'-ACAGT-3' or 5'-TCAGA-3'. The polynucleotide comprising a 3' terminal random multimer segment and a stem-loop form according to the present invention may accordingly comprise the restriction enzyme recognition site 5'-ACAGT-3' or 5'-TCAGA-3'. The site may be provided as single site, or in a multiple form. It is preferred that the site is a single site. According to further embodiments, the restriction enzyme recognition site 5'-ACAGT-3' may be cleaved at the third position to yield 5'-ACA/GT-3', thus providing a 1 nucleotide 3' overhang, more specifically to provide a 1 nucleotide 3' A overhang. According to different embodiments, the restriction enzyme recognition site 5'-TCAGA-3' may be cleaved at the third position to yield 5'-TCA/GA-3', thus providing a 1 nucleotide 3' overhang, more specifically to provide a 1 nucleotide 3' A overhang. Any restriction enzyme recognizing the mentioned sequence and cutting it to yield a 1 nucleotide 3' overhang may be employed within the method of the present invention.

It is preferred that non-DNA nucleotides as described herein above, e.g., 5-methyl-isoC or isoG bases are not part of the restriction enzyme recognition site 5'-ACAGT-3' or 5'-TCAGA-3'.

In further embodiments, the enzyme Hpy188I is used within the method of the present invention to cleave the stem-loop segment. Enzyme Hpy188I is known to recognize the restriction enzyme recognition site 5'-TCAGA-3'. In further alternative embodiments, the enzyme Bst4CI, HpyCH4III or TaaI may be used within the method of the present invention to cleave the stem-loop segment. Enzyme Bst4CI, HpyCH4III and TaaI are known to recognize the restriction enzyme recognition site 5'-ACAGT-3'.

Accordingly, if the stem-loop segment of the polynucleotide comprising a 3' terminal random multimer segment and a stem-loop form according to the present invention comprises the restriction enzyme recognition site 5'-TCAGA-3', the cognate restriction enzyme Hpy188I may be used in the method of the present invention to cleave it. Alternatively, if the stem-loop segment of the polynucleotide comprising a 3' terminal random multimer segment and a stem-loop form according to the present invention comprises the restriction enzyme recognition site 5'-ACAGT-3', the cognate restriction enzyme Bst4CI, HpyCH4III or TaaI may be used in the method of the present invention to cleave it.

The stem-loop segment of the polynucleotide comprising a 3' terminal random multimer segment and a stem-loop form according to the present invention as described above may, in specific embodiments, additionally comprise a barcoding section. The term "barcoding section" as used herein relates to a sequence which is artificially included in the polynucleotide and which serves for identification purposes after the characterization step, e.g., after sequencing. The barcoding segment may, thus, inform the user which of several samples is being characterized, e.g., sequenced. A barcoding section accordingly comprises a unique sequence which is provided only once, i.e., for one molecule/polynucleotide as described above only. The barcoding sequence is preferably different from known naturally occurring sequence motifs. In other embodiments, it is preferably long enough to avoid mix-ups with naturally occurring sequences or different barcoding sequences. According to preferred embodiments, the barcoding sequence has a length of at least 6 to about 12 or more nucleotides. In certain embodiments a barcoding segment may be present once, or multiple times in the polynucleotide of the present invention. If more than one barcoding segment is present, e.g., 2, 3, 4 or 5 or more, the differentiating, i.e., indexing sequence of each segment is different, thus allowing for two or more independent identification processes. Further details would be known to the skilled person, or can be derived from suitable literature sources such as Kozarewa et al., 2011, Methods Mol. Biol. 733, 279-298.

In a further step of the method of the present invention an adaptor polynucleotide complex associated with an RNA translocase enzyme and at least one cholesterol tether segment are connected to the polynucleotide obtained in the previous step, i.e., an RNA polynucleotide associated with a polynucleotide as defined herein above, which has been cleaved in the stem-loop portion of the polynucleotide. The term "adaptor polynucleotide complex" as used herein refers to a complex of non-RNA polynucleotides which comprises, inter alia, a sequence facilitating the entry of an RNA translocase enzyme into a transmembrane pore. In specific embodiments of the present invention the adaptor polynucleotide complex comprises a pair of two at least partially complementary non-RNA polynucleotides. The non-RNA polynucleotide may comprise one or more non-RNA nucleotides; it is preferably a DNA polynucleotide.

The portion of the adaptor complex which is associated with an RNA translocase enzyme may, in certain embodiments, comprise a leader sequence. Typically, the leader sequence threads into the transmembrane pore as described herein. The leader sequence may further comprise additional segments such as one or more spacers. The spacer may, for example, comprise a sequence which is capable of stalling the RNA translocase. It is particularly preferred that the leader sequence comprises a binding site for an RNA translocase enzyme. The term "RNA translocase enzyme binding site" as used herein includes a DNA or DNA analogue sequence of a length which allows one or more RNA translocase enzymes to bind thereto. The length of the binding site typically depends on the number of RNA translocase enzymes that should bind thereto. The region to which a RNA translocase enzyme is capable of binding is preferably a polynucleotide such as DNA, a modified polynucleotide (e.g., an abasic DNA), PNA, LNA, or polyethylene glycol (PEG). Preferably the RNA translocase enzyme binding site is a single stranded, non hybridized region. Accordingly, in preferred embodiments, the adaptor polynucleotide complex is pre-bound to one or more RNA translocases. The term "RNA translocase" as used herein relates to a motor protein, which is capable of interacting with a transmembrane pore as described herein and which accordingly transports a polynucleotide as single stranded entity through the pore, i.e., controls translocation of a polynucleotide as described herein, e.g., an RNA polynucleotide as defined above. Examples of suitable translocases include SF2 helicase, NS3 helicase, NPH-II helicase, Upf1 helicase or RIG-I translocase or derivatives thereof, or a derivative of a DNA helicase such as Hel308 helicase, RecD helicase, XPD helicase or Dda helicase which is capable of translocating RNA polynucleotides.

In further embodiments, the leader sequence may comprise one or more blocking sites which are capable of preventing backwards movements of the RNA translocase enzyme or any slipping off the enzymes from the transmembrane pore.

The adaptor polynucleotide complex may further be associated to or comprise a tether segment. The term "tether segment" as used herein relates to an element which is capable of coupling the adaptor polynucleotide complex and any further element connected to it to a bilayer membrane. The coupling is typically transient and is conveyed by any suitable molecule, preferably a cholesterol entity or a fatty acid, more preferably a cholesterol entity such as a cholesterol-TEG molecule. The coupling accordingly helps to anchor the adaptor polynucleotide complex and its associated elements at or close to the transmembrane pore and thereby allows for an introduction of the RNA polynucleotide to enter the transmembrane pore and to be characterized.

Alternative compounds which can be used to couple to a membrane comprise biotin, thiol, or lipids. The tether typically comprises, besides the coupling functionality, a non-RNA polynucleotides as defined above, which is connected to the coupling entity, e.g. a cholesterol entity. The tether segment may further comprise one or more linker segments, e.g., a portion of variable length, which can be employed to increase the distance between the target RNA polynucleotide and the transmembrane pore to facilitate its characterization. The linker may, in further embodiments, comprise an RNA translocase enzyme binding site as defined herein above.

The connection of the polynucleotide complex to the polynucleotide obtained in the previous step may be performed by annealing and ligating steps. For example, a 5' T overhang of one strand of the adaptor polynucleotide may be annealed to a 3' A overhang in the polynucleotide comprising the stem-loop segment according to the present invention after cleavage with a restriction enzyme as defined herein above. Alternatively, any other suitable connection approach may be used, e.g., chemical attachment via click chemistry or covalent bondings, etc. It is preferred that the connection is performed such that the RNA translocase enzyme is connected to the RNA polynucleotide to be characterized, and that the tether element is connected to the complementary strand, e.g., comprising a part to the stem-loop segment as defined herein above, optionally also comprising a cDNA sequence produced by the reverse transcriptase as described herein above. A schematic overview of the configuration of the complex after the adaptor complex has been connected to the polynucleotide as defined herein and to the target RNA polynucleotide can be derived from FIG. 2, designators 8 and 9. This configuration allows to characterize the target RNA polynucleotide, while any optionally present cDNA strand is preferably not characterized, but is rather provided for stability and conformation reasons.

In a further step of the present method, the modified RNA polynucleotide obtained in the previous step (v) is contacted with a transmembrane pore such that the RNA translocase controls the movement of the RNA polynucleotide through the transmembrane pore and the cholesterol tether anchors the RNA polynucleotide in the vicinity of the transmembrane pore. Typically, the function of a tether anchor as described herein is to bring the molecules to the membrane surface, where the transmembrane pore is located. In this scenario, the characterization of the RNA polynucleotide is facilitated since the transmembrane pore can be reached more easily. The term "transmembrane pore" as used herein relates to a protein spanning a bilayer membrane which comprises an opening which is capable of guiding through a polynucleotide, preferably an RNA or DNA polynucleotide, or an amended version thereof, e.g., comprising one or more non-naturally occurring nucleotides such as isoG or isoC, or derivatives thereof. The transmembrane pore may be any suitable protein. Examples of preferred transmembrane proteins include a protein pore derived from hemolysin, leukocidin, MspA, MspB, MspC, MspD, CsgG, lysenin, outer membrane porin F (OmpF), outer membrane porin G (OmpG), outer membrane phospholipase A, Neisseria autotransporter lipoprotein (NalP) or WZA. Also envisaged are commercially available transmembrane pore proteins such as the pore proteins offered by, or described by, Oxford Nanopore Technology.

In an ultimate step of the present method one or more measurements are taken during the movement of the RNA polynucleotide through the transmembrane pore. The measurements may be indicative of one or more characteristics of the RNA polynucleotide, which allows to characterize the target RNA polynucleotide. The term "measurement" as used herein relates to optical and/or electrical measurements, preferably to electrical measurement at the transmembrane pore. Typically, the current passing through the transmembrane pore is measured as the target RNA polynucleotide or a cDNA polynucleotide complementary to the RNA polynucleotide passes through the transmembrane pore. The measured current is typically indicative for one or more characteristics of the analyzed polynucleotides. The method may, for example, be performed using an apparatus as described in the prior art, e.g., disclosed in principle in WO 2008/102120, or derivatives or modified versions thereof. In general, the methods may be carried out using a patch claim or voltage clamp to detect changes in the current across the transmembrane pore when the polynucleotide is translocated through the pore. The measurement, in certain embodiments, includes the use of a charge carrier such as metal salts, chloride salts, ionic liquids, organic salts, in particular NaCl, KCl, CsCl; further envisaged is the use of a suitable buffer, e.g., HEPES, Tris-HCl, etc.; further envisaged is the use of nucleotides, e.g., AMP, ADP, ATP, dAMP, dADP, dATP, etc. which may be employed for the translocase activity; and enzyme cofactors such as divalent metals ions including Mg2+, $Ca^{2+}$, and $Co^{2+}$.

One of the characteristics of the RNA polynucleotide to be determined according to the present invention is, in one embodiment (i), the length of the RNA polynucleotide. The method further allows for the determination of a cDNA polynucleotide which is optionally provided via reverse transcription, being complementary to the RNA polynucleotide. The length as mentioned above may be measured by counting the number of interactions, i.e., current changes, at the transmembrane pore. Since for every nucleotide passing the pore a current change is expected, the summing up of the interactions provides an indication for the length of the analyzed polynucleotide.

Another characteristic of the RNA polynucleotide to be determined according to the present invention is, in a further embodiment (ii), the identity of the RNA polynucleotide. This feature may, for example, be determined by determining the sequence of the polynucleotide as described herein below, or by determining specific motifs or elements within a polynucleotide allowing to derive the identity of the polynucleotide, e.g., a barcode etc., by scanning for the elements.

Another characteristic of the RNA polynucleotide to be determined according to the present invention is, in a further embodiment (iii), the sequence of the RNA polynucleotide. This feature may, for example, be determined by determining the sequence of the polynucleotide as described in Shaghayegh et al., 2016, J. Phys. D: Appl. Phys. 49, 413001; or in Timp et al., IEEE Trans Nanotechnol., 2010, 9, 3, 281-294. In general, each of the measured nucleotides A, U, G, C passing through the transmembrane pore produces a unique electric current pattern which can be measured, thus representing the sequence of the polynucleotide.

A further characteristic of the RNA polynucleotide to be determined according to the present invention is, in a further embodiment (iv), the presence of a nucleotide modification in the RNA polynucleotide. Typically, specific modification to the RNA polynucleotide will lead to specific current pattern, which can be registered and correlated to the modifications. For example, DNA can be distinguished from RNA on the basis of the different chemical composition of the both entities It is preferred that the characteristic to be determined is the sequence of the target RNA polynucleotide.

In a different aspect, the present invention envisages a method of preparing an RNA polynucleotide for transmembrane sequencing comprising the steps of:

(i) providing an RNA polynucleotide;

(ii) modifying the RNA polynucleotide by annealing and ligating a polynucleotide comprising a 3' terminal random multimer segment and having a stem-loop form;

(iii) optionally performing a reverse transcription of the RNA polynucleotide;

(iv) cleaving the stem-loop segment of the annealed polynucleotide to yield a 3' A overhang; and (v) connecting an adaptor polynucleotide complex associated with an RNA translocase enzyme and at least one cholesterol tether segment to the polynucleotide obtained in step (iv).

The features of the mentioned preparation method correspond to those features defined herein above. The product obtained by the above outlined method for preparing an RNA polynucleotide for transmembrane sequencing may be used for subsequent sequencing activities as explained herein above. The product may, in alternative embodiments, be stored for later steps, or shipped to different locations, etc. Also envisaged are further modification steps which do not directly lead to a characterization of the molecule by transmembrane sequencing. In a specific embodiment, the method of preparing an RNA polynucleotide for transmembrane sequencing may only comprise steps (i) to (iv) as defined herein above. Also envisaged is a method which comprises only steps (i) and (ii) as defined herein above, or steps (i) to (iii) as defined herein above.

In a further aspect, the present invention relates to a kit for characterizing a target RNA polynucleotide comprising a polynucleotide comprising a 3' terminal random multimer segment and having a stem-loop form, wherein the stem-loop form comprises one or more 5-methyl-isoC-isoG base-pairs, preferably comprising a polynucleotide with a 3' terminal random multimer segment and having a stem-loop form as defined in. The features of the method as defined herein above apply also to the kit of the present invention. The kit may, for example, comprise reagents and components as defined in one or more steps of the present methods. For example, the kit may comprise reagents or components for modifying the RNA polynucleotide by annealing and ligating a polynucleotide comprising a 3' terminal random multimer segment and having a stem-loop form as defined above. In a different embodiment, the kit may comprise or may comprise in addition reagents or components for performing a reverse transcription of the RNA polynucleotide. In a further embodiment, the kit may comprise or may comprise in addition reagents or components for cleaving the stem-loop segment of the annealed polynucleotide to yield a 3' A overhang. In a further embodiment, the kit may comprise or may comprise in addition reagents or components for connecting an adaptor polynucleotide complex associated with an RNA translocase enzyme and at least one cholesterol tether segment to the polynucleotide as described herein. In a further embodiment, the kit may comprise or may comprise in addition reagents or components for contacting the modified RNA polynucleotide as defined herein with a transmembrane pore such that the RNA translocase controls the movement of the RNA polynucleotide through the transmembrane pore and the cholesterol tether anchors the RNA polynucleotide in the vicinity of the transmembrane pore. In yet another embodiment, the kit may comprise or may comprise in addition reagents or components taking one or more measurements during the movement of the RNA polynucleotide through the transmembrane pore, wherein the measurements are indicative of one or more characteristics of the RNA polynucleotide, thereby characterizing the target RNA polynucleotide, as defined above. The kit may further comprise two or more of the component or reagent groups as defined above, e.g., components or reagents for performing 2 steps as defined herein, 3 steps as defined herein, 4 steps as defined herein, etc.

The kit may, in general, comprise suitable buffer solutions, labels or washing liquids, etc. Furthermore, the kit may comprise an amount of a known nucleic acid molecule or protein, which can be used for a calibration of the kit or as an internal control. Corresponding ingredients would be known to the skilled person.

Additionally, the kit may comprise an instruction leaflet and/or may provide information as to its usage etc.

Also envisaged is an apparatus performing the above mentioned method steps. The apparatus may, for example, be composed of different modules which can perform one or more steps of the method of the present invention. These modules may be combined in any suitable fashion, e.g., they may be present in a single place or be separated. Also envisaged is the performance of the method at different points in time and/or in different locations. Some steps of the method as defined herein may be followed by breaks or pauses, wherein the reagents or products, etc. are suitably stored, e.g., in a freezer or a cooling device. In case these steps are performed in specific modules of an apparatus as defined herein, the modules may be used as storage vehicles. The modules may further be used to transport reaction products or reagents to a different location, e.g., a different laboratory, etc.

In yet another aspect, the present invention relates to the use of a polynucleotide comprising a 3' terminal random multimer segment and having a stem-loop form, wherein the stem-loop form comprises one or more 5-methyl-isoC-isoG base-pairs for the modification of an RNA polynucleotide, thereby preparing the RNA polynucleotide for a direct RNA sequencing through a transmembrane pore. The features of the method as defined herein above apply also to the use of a polynucleotide comprising a 3' terminal random multimer segment and having a stem-loop form, wherein the stem-loop form comprises one or more 5-methyl-isoC-isoG base-pairs for the modification of an RNA polynucleotide of the present invention.

Turning now to FIG. 1, a schematic illustration of an RNA sequencing approach limited to RNA polynucleotides 1 comprising poly-A-tails, i.e., full length RNA polynucleotides is shown. To these molecules as poly-T-primer 2 is annealed 3. The resultant, partially double stranded molecule 4 can optionally be reverse transcribed 5, resulting in an RNA/cDNA hybrid 6. Subsequently, a sequencing adaptor 7 comprising a translocase and a tether element is ligated 8 to the hybrid 6, resulting in an RNA/cDNA hybrid prepared for sequencing 9. In a next step the RNA/cDNA hybrid prepared for sequencing 9 is translocated 10 to a transmembrane pore 11, where the RNA polynucleotide 1 is characterized, i.e., sequenced. For the first two steps, a time period of approximately 100 minutes is usual (12). For the next steps a time period of 15 minutes is typical (13).

Figure 2:
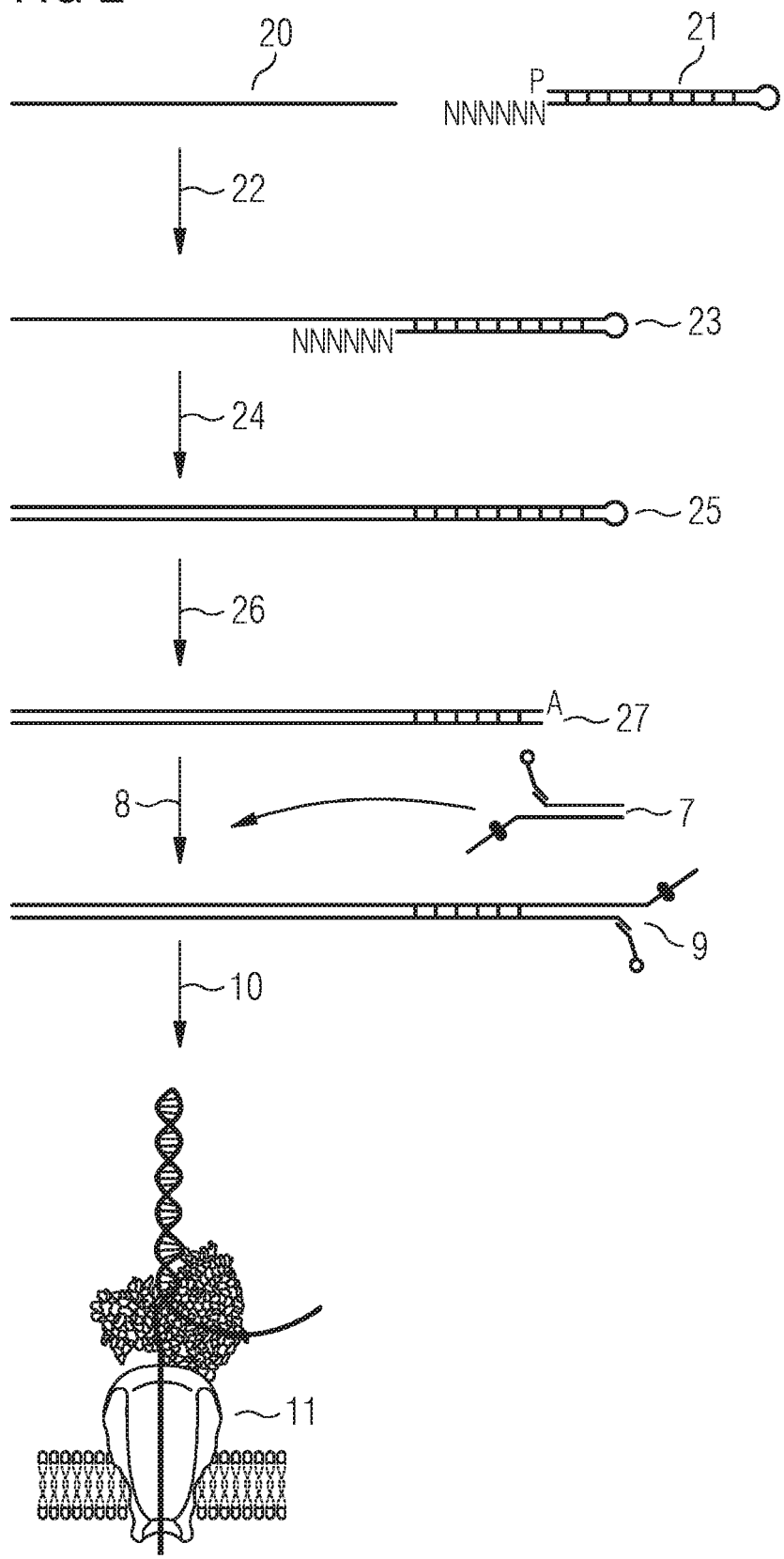
FIG. 2 shows a schematic illustration of the method steps according to an embodiment of the present invention including the employment of a stem-loop form-comprising polynucleotide, the provision of a random multimer, the addition of translocase and tether elements to the molecule and determination of the sequence by translocating through a transmembrane pore.

FIG. 2 shows a schematic illustration of the method steps according to the present invention, which works with all kinds of RNA polynucleotides 20, including poly-A-tail comprising RNA polynucleotides and non-poly-A-tail comprising RNA polynucleotides. To the RNA polynucleotide 20 a stem-loop primer with a random multimer 21 is annealed 22 resulting in a partially double stranded nucleic acid 23. Subsequently, a reverse transcription can optionally be performed 24, resulting in a RNA/cDNA hybrid with stem-loop primer structure 25. In a next step, the stem-loop primer is cleaved 26 with a restriction enzyme to yield a RNA/cDNA hybrid with an A overhang 27. Subsequently, a sequencing adaptor 7 comprising a translocase and tether element 7 is ligated 8 to the hybrid 27, resulting in an RNA/cDNA hybrid prepared for sequencing 9. In final step the RNA/cDNA hybrid prepared for sequencing 9 is translocated 10 to a transmembrane pore 11, where the RNA polynucleotide 20 is characterized, i.e., sequenced.

FIG. 3 shows an example of a stem-loop form-comprising polynucleotide according to an embodiment of the present invention. The stem-loop polynucleotide 21 comprises a loop segment 30, a restriction enzyme recognition site 31, 5-methyl-isoC-isoG base-pairs 32, as well as a random multimer segment 33.

LIST OF REFERENCE NUMERALS

1 RNA polynucleotides comprising poly-A-tails
2 Poly-T-primer
3 Annealing reaction
4 Partially double stranded molecule
5 Reverse transcription reaction
6 RNA/cDNA hybrid
7 Sequencing adaptor comprising a translocase and tether element
8 Ligation reaction
9 RNA/cDNA hybrid prepared for sequencing
10 Translocation to transmembrane pore
11 Transmembrane pore
12 Time period for first two steps
13 Time period for last steps
20 All kinds of RNA polynucleotides
21 Stem-loop primer with a random multimer
22 Annealing reaction with stem-loop primer
23 Partially double stranded nucleic acid comprising the stem-loop primer with a random multimer
24 Reverse transcription reaction starting from stem-loop primer with a random multimer
25 RNA/cDNA hybrid with stem-loop primer structure
26 Cleavage with restriction enzyme in stem-loop primer
27 RNA/cDNA hybrid with an A overhang
30 Loop segment
31 Restriction enzyme recognition site
32 5-methyl-isoC-isoG base-pairs
33 Random multimer segment

---

The invention claimed is:

1. A kit for characterizing a target RNA polynucleotide, the kit comprising a polynucleotide having a stem-loop form and comprising a 3' terminal random multimer segment, a stem portion, and a loop portion, wherein the stem portion comprises one or more 5-methyl-isoC-isoG base-pairs and a restriction enzyme recognition site.

2. A polynucleotide comprising a 3' terminal random multimer segment, a stem portion, and a loop portion, and having a stem-loop form, wherein the stem portion comprises one or more 5-methyl-isoC-isoG base-pairs and a restriction enzyme recognition site.

3. The polynucleotide of claim 2 comprising one or more non-DNA nucleotides.

4. The polynucleotide of claim 2, wherein the 5-methyl-isoC-isoG base-pairs are provided at least at every $4^{th}$, $5^{th}$ or $6^{th}$ position of the stem portion of the polynucleotide.

5. The polynucleotide of claim 2, wherein the 3' terminal random multimer segment is a random hexamer, random heptamer, random octamer, random nonamer or random decamer segment.

6. The polynucleotide of claim 2, wherein the restriction enzyme recognition site comprises the sequence 5'-ACAGT-3' or 5'-TCAGA-3'.

7. The polynucleotide of claim 2, further comprising a barcoding section.

8. The polynucleotide of claim 2, wherein the 5-methyl-isoC-isoG base-pairs are provided at least at every $2^{nd}$ or $3^{rd}$ position of the stem portion of the polynucleotide.

* * * * *